April 18, 1972 H. E. KENDALL Plant Pat. 3,117
AVOCADO TREE
Filed March 9, 1970
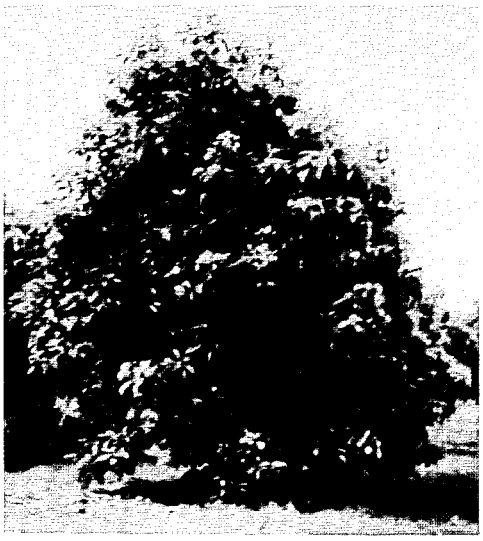
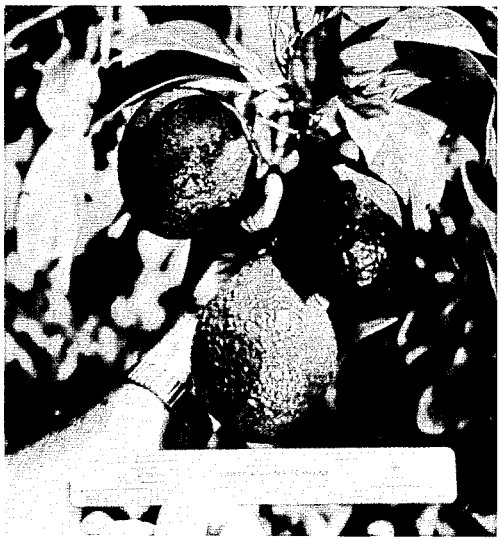
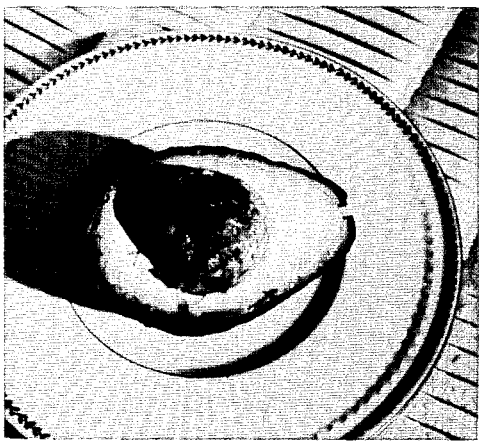
Harold E. Kendall
INVENTOR
BY Clarence A. O'Brien and Harvey R. Jacobson
Attorneys United States Patent Office Plant Pat. 3,117
Patented Apr. 18, 1972

3,117

AVOCADO TREE

Harold E. Kendall, P.O. Box 458,
Goulds, Fla. 33170

Filed Mar. 9, 1970, Ser. No. 17,987
Int. Cl. A01h *5/03*
U.S. Cl. Plt.—44 1 Claim This invention pertains to a new and distinct variety of avocado tree which has many highly desirable characteristics. This new variety originated in my groves in Dade County, Fla., from a seedling of Guatemalan or Guatemalan and West Indian parentage. The new variety has been asexually reproduced in my groves in Dade County, Fla. by budding and grafting without apparent variation.

The accompanying illustrations show a specimen of the fruit, a cross section thereof, and the mature tree.

A description of the new variety follows:

Scientific name: *Persea americana*
Family: Lauraceae
Race: Guatemalan or hybrid of Guatemalan and West Indian
Tree: Extremely fast, upright growing, but branches freely with proper pruning; vigorous, "bushy" appearance and growth. The tree is easily propagated by either the budding or grafting methods.
Leaves: Alternate, light bright green when mature; lanceolate to ovate; margins entire; leaves are narrow.
Fruit: Very bright, shiny, attractive fruit, borne on medium stems 2½" to 2¾" long, singly or in small clusters. Small size, 9 oz. to 13 oz. Medium seed and tight in cavity. Skin pebbled and shiny green. Shape is oblong-ovate. Flesh is light yellow around seed and green next to skin; no fiber; excellent rich, buttery flavor.
Seed: Small to medium size.
Season of bearing: Flowers open in late March and early April. Fruit crop matures in December and early January and fruit can usually be carried on the tree through February. Fruits heavily and regularly each year.

This new variety has been selected for propagation in view of its many desirable qualities.

These include:

(1) A small to medium size fruit which averages 9 to 12 ounces on a tree with average crop and 10 to 13½ ounces on a tree with light crop.

(2) A small to medium size seed which fills the entire seed cavity of the fruit.

(3) Excellent flavored flesh of rich smooth buttery consistency; excellent keeping quality after harvesting and packing which insures wide area marketing possibilities.

(4) Fruit which is bright, shiny and attractive in shape and appearance.

(5) Vigorous growing tree, freely branching and upright in growth.

(6) Early and regular prolific bearer, with fruit maturing in late December and early January, with fruit hanging on the tree usually through the month of February.

Having thus disclosed my invention, I claim:

1. The new and distinct variety of avocado tree, substantially as shown and described, characterized particularly by its vigorous, fast, upright but freely branching growth; a flowering period in late March and early April; its fruit maturing each year in December and early January; the fruit being further characterized as small to medium size and oblong-ovate with flesh of smooth texture free of fibre and excellent buttery flavor No references cited.

ROBERT E. BAGWILL, Primary Examiner